United States Patent [19]

Cheng et al.

[11] Patent Number: 4,950,596

[45] Date of Patent: * Aug. 21, 1990

[54] STABILIZATION OF INTRACELLULAR ENZYMES

[75] Inventors: Roberta C. Cheng, Midland; Norman G. Moll, Sanford; Robert A. Houtchens; Karen M. McCoy, both of Midland, all of Mich.

[73] Assignee: The Dow Chemical Company, Midland, Mich.

[ * ] Notice: The portion of the term of this patent subsequent to Mar. 4, 2002 has been disclaimed.

[21] Appl. No.: 20,407

[22] Filed: Mar. 2, 1987

Related U.S. Application Data

[63] Continuation-in-part of Ser. No. 707,773, Mar. 4, 1985, abandoned.

[51] Int. Cl.$^5$ .................... C12P 19/24; C12N 11/08
[52] U.S. Cl. ........................ 435/94; 435/180; 435/182; 435/188; 435/234
[58] Field of Search ............. 435/94, 180, 182, 188, 435/234

[56] References Cited

U.S. PATENT DOCUMENTS 4,355,105  10/1982  Lantero, Jr. ..................... 435/94
4,675,292   6/1987  Houtchens et al. ............... 435/94

*Primary Examiner*—Robert A. Wax

[57] ABSTRACT

The subject invention concerns a process for stabilizing intact or ruptured microbial cells having glucose isomerase associated therewith. Specifically exemplified is a process for stabilizing glucose isomerase producing cells of a microorganism belonging to the genus Ampullariella. In the invention process the whole or ruptured microbial cells are contacted with a partially carboxyalkylated- or partially phosphonoalkylated-cationic polyelectrolyte, for example, a partially carboxymethylated polyethyleneimine to flocculate and stabilize the cells. The flocculated cells are further stabilized by encapsulation with a partially carboxyalkylated- or partially phosphonoalkylated-cationic polyelectrolyte. The encapsulation can be done prior to or after the flocculated cells are crosslinked. The net effect is manifested by a dramatic increase in the half-life of the glucose isomerase.

46 Claims, 1 Drawing Sheet

STABILIZATION OF INTRACELLULAR ENZYMES

CROSS-REFERENCE TO RELATED U.S. APPLICATION

This application is a continuation-in-part of copending U.S. application Ser. No. 707,773 filed Mar. 4, 1985, now abandoned.

BACKGROUND

Microbe-catalyzed processes are particularly useful in the production of a variety of chemicals known as fine or specialty chemicals. Perhaps the most important commercial use of microbe-catalyzed processes is in the food industry. Exemplary of such processes is the production of high fructose corn syrup (HFCS) catalyzed by immobilized glucose isomerase. This process converts glucose to an approximately equimolar mixture of fructose and glucose; this mixture is referred to as high fructose corn syrup.

The immobilization of an enzyme which catalyzes a microbe-catalyzed process generally gives better yields of desired product and preserves enzyme integrity. Basically, immobilization is the conversion of enzymes from a water-soluble, mobile state to a water-insoluble, immobile state. The immobilization of the enzyme can be done while the enzyme is still in the living microbe (intracellular), or when the enzyme is in the cell-free state; the immobilization techniques will vary in accord with these two enzyme states. Thus, it should be appreciated that immobilization conditions effective for intracellular enzymes will not necessarily be appropriate for extracellular enzymes, and vice versa.

The immobilization of intracellular enzymes is exemplified by the following U.S. patents:

U.S. Pat. No. 3,779,869—Glucose isomerase within bacterial cells can be stabilized by glutaraldehyde treatment.

U.S. Pat. No. 3,935,069—Microbial cells are flocculated in the presence of certain metallic compounds.

U.S. Pat. No. 3,980,521—Microbial cells are concentrated and crosslinked with glutaraldehyde to form a coherent solid product.

U.S. Pat. Nos. 3,989,596; 3,989,597—Microbial cells having enzymes are subjected to flocculation conditions to produce whole cell aggregate which is useful in effecting enzymatic chemical transformations.

U.S. Pat. No. 4,208,482—Microbial cells containing glucose isomerase are mixed with agar.

SUMMARY OF THE INVENTION

In accordance with this invention microbial cells having glucose isomerase associated therewith are stabilized by a process which comprises contacting said microbial cells (intact cells and/or ruptured cells) with a partially carboxyalkylated- or partially phosphonoalkylated-cationic polyelectrolyte whereby the cells are flocculated and, if desired encapsulated. As used herein microbial cells refers to intact (that is, whole) microbial cells having glucose isomerase associated therewith or ruptured microbial cells in which the glucose isomerase is still present with the other cellular materials. It is critical that the polyelectrolyte, for example, a polyamine, be only partially carboxyalkylated or partially phosphonoalkylated in order to realize the surprising benefits of the process. It is necessary that the polyelectrolyte be only partially carboxyalkylated and/or partially phosphonoalkylated in order that the polyelectrolyte after carboxyalkylation or phosphonoalkylation still retains sufficient cationic properties to flocculate the microbial cells and has sufficient unmodified reactive groups (such as, unmodified amino groups) to allow its crosslinking with the microbial cells but contains sufficient carboxyalkyl and/or phosphonoalkyl groups necessary for the stabilization of the glucose isomerase.

An indication of a particular enzyme's stability is its half-life time (referred to herein as the "half-life" or "$t_{\frac{1}{2}}$"), that is, the time at which the enzyme retains only one-half of its initial enzymatic activity, thus it is generally desirable to increase the enzyme half-life. The benefits of the present invention are readily apparent in that the half-life of glucose isomerase-producing microbial cells, disclosed hereinafter, which were contacted with a partially carboxymethylated polyethyleneimine was estimated to be about 1484 hours; whereas, the control, wherein similar microbial cells were contacted with unmodified polyethyleneimine (PEI) had a half-life of about 669 hours. Fully carboxymethylated polyethyleneimine has also been tested. The preparation with fully carboxymethylated PEI had a half-life of about 310 hours.

The partial modification of the polyelectrolyte can be by carboxyalkylation or by phosphonoalkylation, wherein the alkyl of the carboxyalkyl or phosphonoalkyl groups is —$(CH_2)_n$— in which n=1–3 (preferably n=1), or —$(CHR)$—$(CH_2)_n$— wherein R=methyl, ethyl, propyl, or isopropyl, and n=1 or 2.

Further stabilization of the immobilized enzyme (IME) is obtained by encapsulating the immobilized cells with protective layers of polymer(s). In general, encapsulation has been found to give a two-fold increase in glucose isomerase half-life. This added stabilization of glucose isomerase is applicable for processes carried out in a pH range of about 6 to about 8.5, and has particular advantages over untreated glucose isomerase which is generally much less stable at pH's of about pH 6 to about 7.5. The advantages of operating the isomerization process at lower pH, which are well known to HFCS (High Fructose Corn Syrup) producers, are that: (1) it minimizes pH adjustment before and after the isomerization, (2) it reduces by-products formation and thus reduces purification costs, and (3) purer HFCS can be obtained.

As used herein, flocculation refers to a process which involves the use of polyelectrolytes to promote the aggregation of small particles in an aqueous medium. Flocculants have been used successfully to facilitate the isolation of microbial cells from fermentation broths. In the immobilization of cellular materials, for example, cellular materials present in a fermentation broth, flocculation is included in the process in order to simplify the isolation and dehydration of the cellular materials. In addition, additives may be added and coflocculated with the cellular materials to impart desirable properties to the immobilized enzyme preparations. (P. L. Busch and W. Stumn, Environmental Science and Technology, 2, 49–53 (January 1968); and L. L. Gasner and D. I. C. Wang, Biotechnology and Bioengineering, 12, 873–887 (1970)).

Surrounding a particle with a membranous envelope is referred to as encapsulation. In the field of enzymology, microencapsulation of enzyme or enzyme producing organisms has been used as a means of immobilization and enzyme stabilization. Typically, the enzyme is encapsulated in semipermeable membranes. The semipermeable membrane serves as a barrier to prevent the enzyme from leaking out to the substrate solution, and to keep impurities from getting close to the enzyme and accelerating enzyme inactivation. (T. M. S. Chang, Science, 146, 524 (1964)). According to the present invention, the immobilized glucose isomerase (IMGI) is encapsulated by coating, such as by dipping, the immobilized glucose isomerase particles in or with a solution of, for example, a partially carboxymethylated PEI to form a thin membranous envelope which is insolubilized upon crosslinking with a crosslinking agent such as glutaraldehyde.

REFERENCE TO DRAWING

FIG. 1 depicts the preparation of stabilized glucose isomerase in accordance with the present invention.

DETAILED DESCRIPTION OF THE INVENTION

Figure 1:
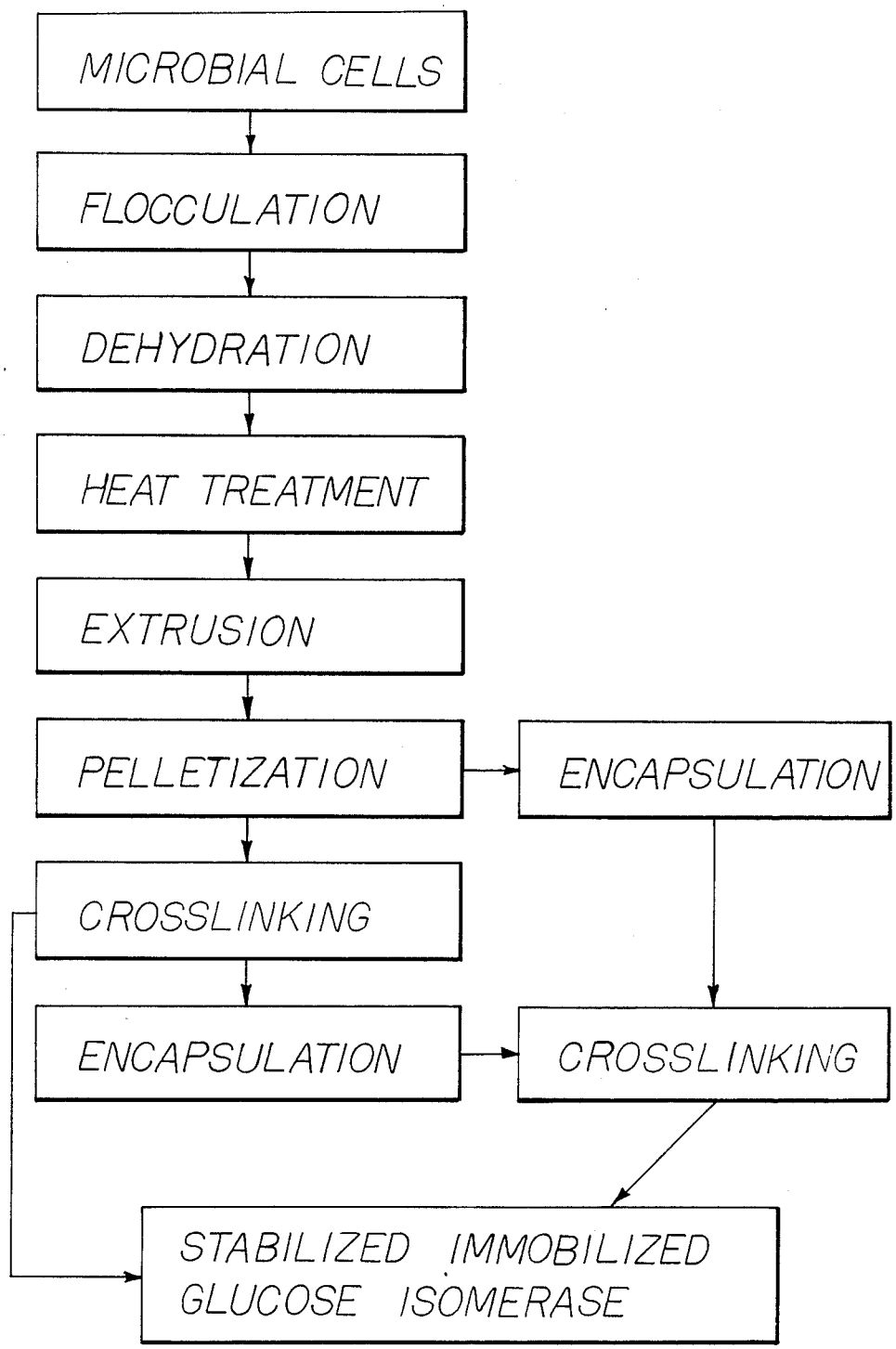

This invention concerns a process to flocculate and stabilize, and, if desired, encapsulate, intact or ruptured microbial cells having active enzymes associated therewith. The process is particularly useful wherein the microbial cells are in an immobilized system. Though immobilization itself is viewed as a stabilization procedure for the intracellular enzyme, the process described herein increases the stability factor, as measured by the half-life of the particular enzyme. The net result is an improved process for using the enzyme in a microbial-catalyzed process.

The process is specifically exemplified herein by being applied to a process for converting glucose to fructose with immobilized glucose isomerase. Similar techniques can be used with microbial cells producing other enzymes. Necessary modifications to accommodate the use of such other microbial cells are well within the skill of those in the microbiological enzyme art.

Glucose isomerase, can be produced by a large number of microbes as disclosed, e.g., in U.S. Pat. No. 4,308,349, Col. 1, lines 26–32. The Ampullariella species described in U.S. Pat. No. 4,308,349 have been found to be especially good producers of glucose isomerase. Other glucose isomerase-producing microbes known to the art and available to the public also can be used for making the glucose isomerase used in the process of this invention.

The intact or ruptured microbial cells having an active enzyme, such as glucose isomerase, associated therewith, are contacted with a partially carboxyalkylated- or partially phosphonoalkylated-cationic polyelectrolyte. The carboxyalkylation of the polyelectrolyte can be accomplished by processes well known in the art. See, e.g., U.S. Pat. No. 3,424,790, which discloses a process for preparing carboxymethylated polyethyleneimine. The phosphonoalkylation of the polyelectrolyte can also be accomplished using well known processes. See, e.g., S. Westerback et al., J. Am. Chem. Soc., 87, 2567–2572 (1965); and K. Moedritzer et al., J. Org. Chem., 31, 1603–1607 (1966). In the carboxyalkylation or phosphonoalkylation, the alkyl of the carboxyalkyl or phosphonoalkyl groups is —$(CH_2)_n$— wherein $n=1-3$ (preferably $n=1$), or —$(CHR)$—$(CH_2)_n$— wherein R=methyl, ethyl, propyl, or isopropyl, and $n=1$ or 2.

The modification of the polyelectrolyte by carboxyalkylation or phosphonoalkylation, when used for flocculation and stabilization, should be such that the polyelectrolyte after carboxyalkylation or phosphonoalkylation retains sufficient cationic properties to flocculate the microbial cells and has sufficient unmodified reactive groups (such as, unmodified amino groups) to allow its crosslinking with the microbial cells but yet contains sufficient carboxyalkyl and/or phosphonoalkyl groups to stabilize the glucose isomerase. Partial carboxyalkylation or partial phosphonoalkylation of the polyelectrolyte, rather than full modification, is necessary in order to have unmodified functionalities present which may electrostatically and/or covalently interact with the cellular material so that the partially modified polyelectrolyte is maintained in proximity to the immobilized glucose isomerase to provide its stabilizing effect. The extent of carboxyalkylation or phosphonoalkylation of the polyelectrolyte may vary depending on factors such as the nature of the polyelectrolyte, the particular glucose isomerase to be stabilized and the conditions under which the glucose isomerase is to be used; however, it will be readily determinable by one skilled in the art employing the teachings hereof. For example, the extent of carboxymethylation of polyethyleneimine (when used for flocculation and stabilization), can be varied from about 0.1 to about 1.0 equivalents of ethyleneimine, preferably from about 0.25 to about 0.5 equivalents of ethyleneimine. This is accomplished by reacting a limited amount of chloroacetic acid (from 0.1 to 1.0 equivalents of the polyethyleneimine, as measured by the total nitrogen content of the polyethyleneimine) with the polyethyleneimine. Thus the fractional number preceding carboxymethylated polyethyleneimine (CM-PEI) found herein represents the stoichiometric ratio of chloroacetic acid to the total nitrogen in the PEI used in the synthesis (that is, the moles of chloroacetic acid to the total moles of nitrogen in the PEI used in the synthesis) of the carboxymethylated polyethyleneimine; the aforementioned ratio is frequently indicated herein as "CM:N".

Polyelectrolytes which can be partially carboxyalkylated or partially phosphonoalkylated as disclosed above, are classified as cationic polyelectrolytes, for example, polyamines (primary, secondary, and tertiary amines); polyaminoacids, for example, polylysine; cationic polyacrylamides, for example, polydimethylaminopropylmethacrylamide; cationic poly(vinyl chloride), for example, poly(vinyl chloride) aminated with triethylene tetraamine; cationic copolymers, for example, styrene dimethylaminopropylmethacrylamide (50:50) copolymer; and cationic flocculants, for example, Purifloc C-31 (Trademark of The Dow Chemical Company) which is a polyamine polymer prepared by reacting ethylenedichloride with a mixture of ethyleneimine oligomers.

When used in an immobilized cell system, the partially carboxyalkylated- or partially phosphonoalkylated-cationic polyelectrolyte can be incorporated into the immobilized system, for example, either by incorporating it electrostatically (via, flocculation) or by covalently incorporating it into the immobilized cell system via a crosslinking agent such as glutaraldehyde. Thus, it is physically separated from the feed and product. This feature, advantageously, eliminates the need for removal of the carboxyalkylated- or phosphonoalkylated-cationic polyelectrolyte from the final product. Also, since the carboxyalkylated- or phosphonoalkylated-cationic polyelectrolyte is "built into" the immobilized system, no pretreatment of the feed with stabilizing photoelectrolyte is required; this minimizes the operating cost in using the immobilized system.

Another advantageous aspect of the invention process can be shown when applied to immobilized glucose isomerase systems. The process provides a glucose isomerase which has enhanced stability over a pH range of about 6 to about 8.5; the stability is greater than for either of two well known commercial products, as shown in Table I.

The partially carboxyalkylated- or partially phosphonoalkylated-cationic polyelectrolyte, as exemplified by CM-PEI, stabilized immobilized enzyme system also is less sensitive to impurities present in the feed. Furthermore, encapsulation of the immobilized cells further enhances the stability of the glucose isomerase. The encapsulation can be performed on either the flocculated cells (sometimes referred to herein as "particles") or the flocculated-crosslinked cells. The polymers (that is, polyelectrolytes) which can be used to encapsulate the microbial cells are the same as described herein for flocculating the microbial cells, except that the polyelectrolyte used for encapsulation can be more highly carboxyalkylated or phosphonoalkylated than that used for flocculating the microbial cells; the polyelectrolyte used for encapsulation can be more highly modified since the cationic property is no longer essential (as is necessary for flocculation), however, (after carboxyalkylation or phosphonoalkylation) there still must be sufficient reactive groups left to permit crosslinking, via a crosslinking agent, to effectively stabilize the encapsulated particles. For example, for the carboxymethylation of polyethyleneimine, when used for encapsulation, the carboxymethylation can be varied from about 0.2 to about 1.0 equivalents of ethyleneimine, preferably from about 0.4 to about 0.75 equivalents of ethyleneimine.

Crosslinking agents that may be employed in the practice of the invention include any difunctional and/or multifunctional reagent that is reactive towards amino groups, such as, aldehydes, for example, glutaraldehyde, glyoxal, dialdehyde starch and polyglutaraldehyde; isocyanates, for example, toluene-2,4-diisocyanate, hexamethylene-diisocyanate and diphenylmethane-diisocyanate; thioisocyanates, for example, hexamethylene-diisothiocyanate; anhydrides, e.g., polymethacrylic anhydride and poly-(ethylenemaleic anhydride); water soluble carbodiimides, e.g., 1-cyclohexyl-3-(2-morpholinoethyl) carbodiimide; chlorotriazines, e.g., cyanuric chloride; diazo compounds, e.g., bisdiazobenzidine-3,3'-disulfonate and tetraazotized-O-dianisidine; difluorobenzenes, e.g., 1,3-difluoro-4,6-dinitrobenzene; epoxy compounds, e.g., epichlorohydrin; phosgene derivatives, e.g., ethyl chloroformate; and halogenoalkyl derivatives, e.g., bromoacetylbromide.

The immobilized enzyme catalyst is prepared in suitably sized particles, for example, cylindrical particles with a diameter of about 500 to about 840 microns and ranging in length from about 0.1 to about 0.2 inches. The particles can be prepared to have sufficient structural stability to allow continuous operation in column reactors for 2000 hours or longer.

Several of the advantageous aspects of the invention process, as exemplified by partially carboxymethylated PEI is that it: (1) flocculates the microbial cells and glucose isomerase very well; (2) contains groups, for example, (—HN—CH$_2$—COOH) groups effective in stabilizing glucose isomerase; and (3) contains amine functionalities to allow covalent crosslinking of the flocculant with the cellular materials.

Following are examples that illustrate the process and products of the invention. All percentages are by weight and all solvent mixture proportions are by volume unless otherwise noted. All calculations concerning polyethyleneimine are based on 43 as the molecular weight for each ethyleneimine unit.

EXAMPLE 1

Flocculation

A suspension of whole cells of Ampullariella 3876, ATCC 31351, (500 ml; containing 3.31 percent solids (dry weight)) was adjusted to pH 8.0 with 5N potassium hydroxide. To this was added 120 ml of a carboxymethylated polyethyleneimine, (CM:N=0.25, at pH 7.0, containing 0.019 equivalent of nitrogen/100 ml) with vigorous stirring for one minute, followed by gentle stirring for 5 more minutes. The flocculated cells were collected in an IEC chemical centrifuge basket (IEC #1303, 5 inch diameter×2½ inch depth) (International Equipment Company, Needham Ht., Mass.) at 5200 revolutions per minute (rpm), and washed with 1500 milliliters (ml) of Milli-Q water (Trademark of Millipore Corp., Milford, Mass., for highly purified water). The cell paste was then heat-treated at 70° C. for 1 hour. The heat-treated cells (containing approximately 30 to 40 percent solid) were extruded through a 0.03 inch (internal diameter) exit tubing on a French press (American Instrument Co., Silver Spring, Md.) at 4000 pounds per square inch (psi) and into 800 ml of acetone. After being dehydrated in the acetone bath for 1 hour, the extrudates were collected and further dried in a vacuum oven for 2–3 hours at room temperature to remove the residual acetone, and then were pelletized in a Waring blender (3×5 second pulses), and sieved. The particles of 500–840 microns were used for crosslinking and testing.

Crosslinking

Cell particles were weighed (7 grams (g)) into 42 ml of a glutaraldehyde solution (containing 4.2 ml of 25 percent glutaraldehyde, 16.8 ml of water and 21 ml of 0.2M potassium phosphate) at pH 8.0. This was incubated at 25° C and 200 rpm in a shaker bath for 1 hour. The resulting crosslinked particles were collected on a sintered glass (coarse) funnel and washed 3 times with Milli-Q water (3×200 ml) and dried in a vacuum oven at room temperature for 24 hours. The particles were again sieved and the 500–840 micron fraction was used for column studies. Glucose isomerase activity of the immobilized glucose isomerase determined by batch assay in a substrate containing 5 percent glucose, 50 mM Mg$^{++}$ (MgSO$_4$ was used) and 1 mM Co$^{++}$ (CoCl$_2$ was used) in 0.25M maleate buffer at pH 6.5 and 70° C., was 63±3 GIU/g (1 GIU is defined as the glucose isomerase activity which catalyzes the isomerization of 1 micromole of glucose to fructose per minute under standard assay conditions).

Stability (half-life time (t½)) of the immobilized enzyme was determined in continuous upflow column reactors (9×150 millimeters (mm)) at 60° C., with a flow rate of 30 ml/hour, and residence time of approximately 20 minutes. The substrate used for the study contained 50 percent (W/V) glucose, 3 millimolar (mM) Mg$^{++}$, similar to that used by high fructose corn syrup producers. Sodium azide (0.02 percent) was added as an antimicrobial. The half-life of the 0.25 CM-PEI flocculated and glutaraldehyde crosslinked cells of Ampullariella 3876 at pH 8.2 was estimated to be 1484 hours, compared to a t½ of 669 hours (hrs) for the control, which was prepared similarly, using PEI-600 (Cordova Chemical Company, Muskegon, Mich.), a polyethyleneimine product, as the flocculant. See Table II.

EXAMPLE 2

Whole cells of Ampullariella 3876 were flocculated with a CM-PEI (CM:N=0.5; 6 percent based on the dry weight of the bacterial cells), and crosslinked with 15 percent glutaraldehyde as described above. The immobilized glucose isomerase thus prepared had a t½ of 958 hours.

The glucose isomerase catalyst prepared in the above examples is dark brown in color, and cylindrical in shape. The particle size is about 500 to 840 microns in diameter and greater than 0.1 inch in length. It possesses sufficient physical stability to allow continuous operation for over 2000 hours in column reactors.

EXAMPLE 3

Upon flocculating the whole cells of Ampullariella 3876 with a fully carboxymethylated PEI (CM:N=2.0; 6 percent based on the dry weight of the bacterial cells), and crosslinking with fifteen percent glutaraldehyde according to the procedure disclosed in Examples 1 and 2, there was obtained an immobilized glucose isomerase having inferior stability compared to the partially carboxymethylated PEI flocculated and crosslinked Ampullariella 3876 described in Examples 1 and 2. The t½ was estimated to be 310 hours at pH 8.2.

EXAMPLE 4

Whole cells of Ampullariella 3876 were flocculated with 6 percent flocculants (based on the total dry weight of the cellular material) listed in Table III and crosslinked with 15 percent glutaraldehyde in the same manner as described in Example 1. Half-life time (summarized in Table III) of the immobilized cells of Ampullariella 3876 thus obtained were determined at pH 6.6 and 60° C. in similar fashion to Example 1.

EXAMPLE 5

Encapsulation Prior to Crosslinking

Particles prepared as described in Example 1 in the section entitled "Flocculation" were soaked in a solution of partially carboxymethylated PEI (CM:N=0.4), equivalent to 6 percent PEI per gram of cellular material. The bulk of the water was removed by evaporation and lyophilization overnight, and the encapsulated and flocculated cell particles were crosslinked with glutaraldehyde as follows:

Crosslinking—Five grams of the encapsulated particles were weighed into 15 ml of a crosslinking solution containing 0.75 grams of glutaraldehyde in 0.1M of potassium phosphate buffer at pH 8.0. This was incubated at 25° C. and 200 rpm on a shaker for 1 hour. Upon completion, it was washed with Milli-Q water (3×100 ml) and dried thoroughly in a vacuum oven. The particles were again sieved and the fraction of 500-840 microns was used for stability study in the column reactor.

Stability study—Four grams of the immobilized glucose isomerase preparation was immersed in the glucose substrate (50 percent cerelose dextrose [W/V] containing 3 mM $MgSO_4$, and 0.02 percent sodium azide at pH 6.6). After 2 hours, it was packed into a Teflon column (0.5×12 inch), and the half-life time (t½) of the immobilized glucose isomerase was determined in a continuous upflow process with the 50 percent glucose solution, assuming pseudo-first order kinetics for the enzyme inactivation. The effect of partially carboxymethylated PEI encapsulation on the stability of immobilized cells of Ampullariella 3876 is shown in Table IV.

EXAMPLE 6

Encapsulation after Crosslinking

A sample (4.0 grams) of 0.25 CM-PEI flocculated and glutaraldehyde crosslinked Ampullariella 3876, prepared as described in Example 1, was encapsulated with a partially carboxymethylated PEI (CM:N=0.4; equivalent to 0.24 g of PEI), as described in Example 5. The encapsulated immobilized glucose isomerase was crosslinked with 5 percent glutaraldehyde in 0.1M potassium phosphate buffer at pH 8.0 for 30 minutes. The stabilities of the treated as well as the untreated immobilized glucose isomerase (IMGI) were tested in the usual manner. The t½ of the treated was 1018 hours compared to 350 hours for the 0.25 CM-PEI flocculated, but not encapsulated, glucose isomerase in the 50 percent glucose substrate at pH 6.6 and 60° C.

EXAMPLE 7

Encapsulation of Commercially Available Enzyme

A sample (3 grams) of Novo Sweetzyme Q (Trademark of Novo Industries A/S, Bagsvaerd, Denmark, for a glucose isomerase preparation) was immersed in 12 ml of a partially carboxymethylated PEI solution (CM:N=0.4) containing 0.18 grams of PEI at pH 7. The excess liquid was evaporated under nitrogen, and the bulk of the water was removed by lyophilization overnight. The Sweetzyme Q particles encapsulated with CM-PEI were then crosslinked with glutaraldehyde according to the procedure described in Example 1, except that only 5 percent glutaraldehyde was used, and the reaction time was shortened to 30 minutes. Stability of the CM-PEI encapsulated Sweetzyme Q was determined in continuous upflow column reactors (9×150 mm) at 60° C., with a flow rate of 30 ml/hour, and residence time of approximately 20 minutes. The substrate used for the study contains 50 percent (W/V) glucose, 3 mM $Mg^{++}$, similar to that used by high fructose corn syrup producers. Sodium azide (0.02 percent) is added as an antimicrobial. The t½ in the 50 percent glucose substrate at pH 6.6 and 60° C. was 291 hours, compared with 70–115 hours for the untreated Sweetzyme Q.

EXAMPLE 8

Encapsulation of Another Commercially Available Enzyme

A sample (2 grams) of Taka-Sweet (Trademark of Miles Laboratories, Inc., Elkhart, Ind., for a glucose isomerase preparation) was treated with 8 ml of a partially carboxymethylated PEI solution (CM:N=0.4), equivalent to 0.12 grams of PEI at pH 7, according to the previous example. The t½ determined in a column reactor was 725 hours compared to 333–406 hours for the untreated Taka-Sweet in 50 percent glucose substrate at pH 6.6 and 60° C.

EXAMPLE 9

D-glucose is converted to D-fructose in an aqueous medium by contacting the D-glucose with glucose isomerase, prepared as described in the above examples. Operable temperature and pH ranges generally vary from about 45° C. to about 85° C. and from about pH 6 to about 8.5, respectively. The produced D-fructose is recovered by procedures well known in the art.

TABLE I

Half-Life Time of Immobilized Glucose Isomerase at Various pH's and 60° C.

| IME | t ½ (hrs) at pH | | |
|---|---|---|---|
| | 6.6 | 7.4 | 8.2 |
| 0.625 CM-PEI Encapsulated and 0.25 CM-PEI Flocculated Amp* | 1042 | — | 1540 |
| 0.25 CM-PEI Flocculated Amp* | 352 | 1248 | 1484 |
| Novo Sweetzyme Q** | 147 | 452 | 1490 |
| G. B. Maxazyme*** | 130 | 325 | 1143 |

Substrate was 50 percent glucose (W/V) containing 3 mM $Mg^{++}$ and 0.02 percent sodium azide.
*Ampullariella 3876
**Trademark of Novo Industries A/S Bagsvaerd, Denmark
***Trademark of Gist-Brocades NV, Holland

TABLE II

Stability of Partially Carboxymethylated Polyethyleneimine Flocculated and Glutaraldehyde Crosslinked Cells of Ampullariella 3876 at pH 8.2 and 60° C.

| Ratio of CM to Nitrogen | First t ½, Hrs |
|---|---|
| 0 | 669 |
| 0.25 | 1484 |
| 0.5 | 1181 |
| 1.0 | 983 |
| 2.0 | 310 |

TABLE III

Stability Comparison of Immobilized Ampullariella 3876 with Various Flocculants at pH 6.6 and 60° C.

| Flocculants | First t ½, Hrs |
|---|---|
| PEI | 156 |
| 0.25 CM-PEI | 352 |
| 0.4 CM-PEI | 357 |
| 0.5 CM-PEI | 683 |
| Purifloc C-31 | 221 |
| 0.25 CM-Purifloc C-31 | 329 |
| 0.15 CM-Purifloc C-31 | 298 |

TABLE IV

Effect of Partially Carboxymethylated PEI Encapsulation on the Stability (Measured as t ½) of Immobilized Cells of Ampullariella 3876 at pH 6.6 and 60° C.

| Flocculant | Encapsulation | Half-Life, Hrs |
|---|---|---|
| 6% 0.25 CM-PEI | None | 352 |
| 6% 0.25 CM-PEI | 6% 0.625 CM-PEI | 914 |
| 6% 0.2 CM-PEI | 6% 0.4 CM-PEI | 855 |
| 6% 0.2 CM-PEI | 6% 0.625 CM-PEI | 849 |
| 6% 0.2 CM-PEI | 6% 0.5 CM-PEI | 679 |
| 6% 0.25 CM-PEI | 9% 0.625 CM-PEI | 928 |
| 6% 0.25 CM-PEI | 18% 0.625 CM-PEI | 1042 |
| 6% Purifloc C-31* | None | 221 |
| 6% Purifloc C-31 | 6% 0.4 CM-PEI | 677 |
| 6% Purifloc C-31 | 12% 0.4 CM-PEI | 1087 |
| 6% Purifloc C-31 | 18% 0.4 CM-PEI | 1047 |
| 6% 0.25 CM-Purifloc C-31 | None | 329 |
| 6% 0.25 CM-Purifloc C-31 | 6% 0.625 CM-PEI | 1131 |
| 6% 0.15 CM-Purifloc C-31 | None | 298 |
| 6% 0.15 CM-Purifloc C-31 | 6% 0.625 CM-PEI | 819 |
| Purifloc C-31 | | |

*Trademark of The Dow Chemical Company, Midland, Michigan from which the product can be purchased. Purifloc C-31 is a polyamine polymer prepared by reacting ethylenedichloride with a mixture of ethyleneimine oligomers.
Note: All the immobilized cells were crosslinked with glutaraldehyde in the final step before testing stability.
The percentages given in Table IV represent the weight percent of modified PEI based on the dry weight of cellular material.

What is claimed is:

1. A process for stabilizing intact or ruptured glucose isomerase-producing microbial cells having high glucose isomerase associated therewith which comprise
   (1) flocculating said microbial cells with a partially carboxyalkylated- or partially phosphonoalkylated-cationic polyelectrolyte having a positive charge carried by a nitrogen atom to obtain flocculated microbial cells,
   (2) crosslinking said flocculated microbial cells to obtain flocculated-crosslinked microbial cells,
   (3) encapsulating said flocculated-crosslinked microbial cells with a partially carboxyalkylated-or partially phosphonoalkylated-cationic polyelectrolyte having a positive-charge carried by a nitrogen atom to obtain encapsulated microbial cells, and
   (4) crosslinking said encapsulated microbial cells.

2. The process of claim 1 wherein said glucose isomerase-producing microbial cells belong to the genus Ampullariella.

3. The process of claim 2 wherein said Ampullariella glucose isomerase-producing cells are Ampullariella species 3876, the crosslinking is accomplished using glutaraldehyde as a crosslinking agent, and the partially carboxyalkylated- or partially phosphonoalkylated-cationic polyelectrolyte is partially carboxymethylated polyethyleneimine.

4. The process of claim 1 wherein said partially carboxyalkylated- or partially phosphonoalkylated-cationic polyelectrolyte is a partially carboxyalkylated- or partially phosphonoalkylated-polyamine.

5. The process of claim 1 wherein the alkyl of the carboxyalkyl or phosphonoalkyl groups of the partially carboxyalkylated- or partially phosphonoalkylated-cationic polyelectrolyte is —$(CH_2)_n$— wherein n=1–3, or —(CHR)—$(CH_2)_n$— wherein R=methyl, ethyl, propyl or isopropyl, and n=1 or 2.

6. The process of claim 4 wherein said partially carboxyalkylated- or partially phosphonoalkylated-polyamine is partially carboxymethylated polyethyleneimine which is carboxymethylated in the range of about 0.1 to about 1.0 equivalents of ethyleneimine when used for flocculation and carboxymethylated in the range of about 0.2 to about 1.0 equivalents of ethyleneimine when used for encapsulation.

7. A process for stabilizing intact or ruptured glucose isomerase-producing microbial cells having glucose isomerase associated therewith which comprises
   (1) flocculating said microbial cells with a partially carboxyalkylated- or partially phosphonoalkylated-cationic polyelectrolyte having a positive charge carried by a nitrogen atom to obtain flocculated microbial cells,
   (2) encapsulating said flocculated microbial cells with a partially carboxyalkylated- or partially phosphonoalkylated-cationic polyelectrolyte having a positive charge carried by a nitrogen atom, and (3) crosslinking said encapsulated flocculated microbial cells.

8. The process of claim 7 wherein said glucose isomerase-producing microbial cells belong to the genus Ampullariella.

9. The process of claim 8 wherein said Ampullariella glucose isomerase-producing cells are Ampullariella species 3876, the crosslinking is accomplished using glutaraldehyde as a crosslinking agent, and the partially carboxyalkylated- or partially phosphonoalkylated-cationic polyelectrolyte is partially carboxymethylated polyethyleneimine.

10. The process of claim 7 wherein said partially carboxyalkylated- or partially phosphonoalkylated-cationic polyelectrolyte is a partially carboxyalkylated- or partially phosphonoalkylated-polyamine.

11. The process of claim 7 wherein the alkyl of the carboxyalkyl or phosphonoalkyl groups of the partially carboxyalkylated- or partially phosphonoalkylated-cationic polyelectrolyte is $-(CH_2)_n-$ wherein n=1–3, or $-(CHR)-(CH_2)_n-$ wherein R=methyl, ethyl, propyl or isopropyl, and n=1 or 2.

12. The process of claim 10 wherein said partially carboxyalkylated- or partially phosphonoalkylated-polyamine is partially carboxymethylated polyethyleneimine which is carboxymethylated in the range of about 0.1 to about 1.0 equivalents of ethyleneimine when used for flocculation and carboxymethylated in the range of about 0.2 to about 1.0 equivalents of ethyleneimine when used for encapsulation.

13. A process for stabilizing intact or ruptured glucose-isomerase producing microbial cells having glucose isomerase associated therewith which comprises flocculating said microbial cells by contacting said microbial cells with a partially carboxyalkylated- or partially phosphonoalkylated-cationic polyelectrolyte having a positive charge carried by a nitrogen atom.

14. The process of claim 13 wherein said glucose isomerase-producing microbial cells belong to the genus Ampullariella.

15. The process of claim 14 wherein said Ampullariella glucose isomerase-producing cells are Ampullariella species 3876, and the partially carboxyalkylated- or partially phosphonoalkylated-cationic polyelectrolyte is partially carboxymethylated polyethyleneimine.

16. The process of claim 13 wherein said partially carboxyalkylated- or partially phosphonoalkylated-cationic polyelectrolyte is a partially carboxyalkylated- or partially phosphonoalkylated-polyamine.

17. The process of claim 13 wherein the alkyl of the carboxyalkyl or phosphonoalkyl groups of the partially carboxyalkylated- or partially phosphonoalkylated-cationic polyelectrolyte is $-(CH_2)_n-$ wherein n=1–3, or $-(CHR)-(CH_2)_n-$ wherein R=methyl, ethyl, propyl or isopropyl, and n=1 or 2.

18. The process of claim 16 wherein said partially carboxyalkylated- or partially phosphonoalkylated-polyamine is partially carboxymethylated polyethyleneimine which is carboxymethylated in the range of about 0.1 to about 1.0 equivalents of ethyleneimine.

19. Immobilized glucose isomerase comprising flocculated and crosslinked intact or ruptured glucose isomerase-producing microbial cells having glucose isomerase associated therewith wherein said microbial cells are flocculated with a partially carboxyalkylated- or partially phosphonoalkylated-cationic polyelectrolyte having a positive charge carried by a nitrogen atom and then crosslinked.

20. Immobilized glucose isomerase of claim 19 wherein said partially carboxyalkylated- or partially phosphonoalkylated-cationic polyelectrolyte is a partially carboxyalkylated- or partially phosphonoalkylated-polyamine.

21. Immobilized glucose isomerase of claim 20 wherein said partially carboxyalkylated- or partially phosphonoalkylated-polyamine is partially carboxymethylated polyethyleneimine.

22. Immobilized glucose isomerase of claim 21 wherein the crosslinking is accomplished using glutaraldehyde as a crosslinking agent.

23. Immobilized glucose isomerase of claim 19 wherein the flocculated and crosslinked microbial cells are encapsulated with a partially carboxymethylated polyethyleneimine and crosslinked.

24. Immobilized glucose isomerase comprising flocculated intact or ruptured glucose isomerase-producing microbial cells having glucose isomerase associated therewith encapsulated with a partially carboxyalkylated- or partially phosphonoalkylated-cationic polyelectrolyte having a positive charge carried by a nitrogen atom and then crosslinked.

25. Immobilized glucose isomerase of claim 24 wherein said partially carboxyalkylated- or partially phosphonoalkylated-cationic polyelectrolyte is a partially carboxyalkylated- or partially phosphonoalkylated-polyamine.

26. Immobilized glucose isomerase of claim 25 wherein said partially carboxyalkylated- or partially phosphonoalkylated-polyamine is partially carboxymethylated polyethyleneimine.

27. Immobilized glucose isomerase of claim 26 wherein the crosslinking is accomplished using glutaraldehyde as a crosslinking agent.

28. Immobilized glucose isomerase of claim 24 wherein said glucose isomerase is produced by microbial cells belonging to the genus Ampullariella, and the microbial cells are flocculated with a partially carboxymethylated polyethyleneimine.

29. A process for preparing D-fructose from D-glucose which comprises contacting D-glucose with glucose isomerase-producing intact or ruptured microbial cells which have been (1) flocculated with a partially carboxyalkylated- or partially phosphonoalkylated-cationic polyelectrolyte having a positive charge carried by a nitrogen atom, and (2) crosslinked.

30. The process of claim 29 wherein said partially carboxyalkylated- or partially phosphonoalkylated-cationic polyelectrolyte is a partially carboxyalkylated- or partially phosphonoalkylated-polyamine.

31. The process of claim 29 wherein the alkyl of the carboxyalkyl or phosphonoalkyl groups of the partially carboxyalkylated- or partially phosphonoalkylated-cationic polyelectrolyte is $-(CH_2)_n-$ wherein n=1–3, or $-(CHR)-(CH_2)_n-$ wherein R=methyl, ethyl, propyl or isopropyl, and n=1 or 2.

32. The process of claim 30 wherein said partially carboxyalkylated- or partially phosphonoalkylated-polyamine is partially carboxymethylated polyethyleneimine.

33. The process of claim 29 wherein said glucose isomerase-producing microbial cells belong to the genus Ampullariella.

34. The process of claim 33 wherein said Ampullariella species 3876, the crosslinking is accomplished using glutaraldehyde as a crosslinking agent, and the partially carboxyalkylated- or partially phosphonoalkylated-cationic polyelectrolyte is partially carboxymethylated polyethyleneimine.

35. A process for preparing D-fructose from D-glucose which comprises contacting D-glucose with glucose isomerase-producing intact or ruptured microbial cells which have been (1) flocculated with a partially carboxyalkylated- or partially phosphonoalkylated-cationic polyelectrolyte having a positive charge carried by a nitrogen atom, (2) crosslinked, (3) encapsulated with a partially carboxyalkylated- or partially phosphonoalkylated-cationic polyelectrolyte having a positive charge carried by a nitrogen atom, and (4) crosslinked.

36. The process of claim 35 wherein said partially carboxyalkylated- or partially phosphonoalkylated-cationic polyelectrolyte is a partially carboxyalkylated- or partially phosphonoalkylated-polyamine.

37. The process of claim 35 wherein the alkyl of the carboxyalkyl or phosphonoalkyl groups of the partially carboxyalkylated- or partially phosphonoalkylated-cationic polyelectrolyte is —(CH$_2$)$_n$— wherein n=1–3, or —(CHR)—(CH$_2$)$_n$— wherein R=methyl, ethyl, propyl or isopropyl, and n=1 or 2.

38. The process of claim 36 wherein said partially carboxyalkylated- or partially phosphonoalkylated-polyamine is partially carboxymethylated polyethyleneimine.

39. The process of claim 35 wherein said glucose isomerase-producing microbial cells belong to the genus Ampullariella.

40. The process of claim 39 wherein said Ampullariella glucose isomerase-producing cells are Ampullariella species 3876, the crosslinking is accomplished using glutaraldehyde as a crosslinking agent, and the partially carboxyalkylated- or partially phosphonoalkylated-cationic polyelectrolyte is partially carboxymethylated polyethyleneimine.

41. A process for preparing D-fructose from D-glucose which comprises contacting D-glucose with glucose isomerase-producing intact or ruptured microbial cells which have been (1) encapsulated with a partially carboxyalkylated- or partially phosphonoalkylated-cationic polyelectrolyte having a positive charge carried by a nitrogen atom, and (2) crosslinked.

42. The process of claim 41 wherein said partially carboxyalkylated- or partially phosphonoalkylated-cationic polyelectrolyte is a partially carboxyalkylated- or partially phosphonoalkylated-polyamine.

43. The process of claim 41 wherein the alkyl of the carboxyalkyl or phosphonoalkyl groups of the partially carboxyalkylated- or partially phosphonoalkylated-cationic polyelectrolyte is —(CH$_2$)$_n$— wherein n=1–3, or —(CHR)—(CH$_2$)$_n$— wherein R=methyl, ethyl, propyl or isopropyl, and n=1 or 2.

44. The process of claim 42 wherein said partially carboxyalkylated- or partially phosphonoalkylated-polyamine is partially carboxymethylated polyethyleneimine.

45. The process of claim 41 wherein said glucose isomerase-producing microbial cells belong to the genus Ampullariella.

46. The process of claim 45 wherein said Ampullariella glucose isomerase-producing cells are Ampullariella species 3876, the crosslinking is accomplished using glutaraldehyde as a crosslinking agent, and the partially carboxyalkylated- or partially phosphonoalkylated-cationic polyelectrolyte is partially carboxymethylated polyethyleneimine.

* * * * *